(12) United States Patent
Kamei

(10) Patent No.: US 9,394,265 B2
(45) Date of Patent: Jul. 19, 2016

(54) METHOD FOR PRODUCING ALKYLDIOL MONOGLYCIDYL ETHER

(75) Inventor: Junichi Kamei, Chiba (JP)

(73) Assignee: HITACHI CHEMICAL COMPANY, LTD., Tokyo (JP)

( * ) Notice: Subject to any disclaimer, the term of this patent is extended or adjusted under 35 U.S.C. 154(b) by 0 days.

(21) Appl. No.: 14/234,182

(22) PCT Filed: Jul. 17, 2012

(86) PCT No.: PCT/JP2012/068115
§ 371 (c)(1),
(2), (4) Date: Jan. 22, 2014

(87) PCT Pub. No.: WO2013/015156
PCT Pub. Date: Jan. 31, 2013

(65) Prior Publication Data
US 2014/0163246 A1    Jun. 12, 2014

(30) Foreign Application Priority Data
Jul. 22, 2011   (JP) ............................... P2011-160629

(51) Int. Cl.
*C07D 301/27*  (2006.01)
*C07D 301/28*  (2006.01)
*C07D 303/26*  (2006.01)

(52) U.S. Cl.
CPC ............ *C07D 301/28* (2013.01); *C07D 303/26* (2013.01)

(58) Field of Classification Search
CPC . C07D 3303/26; C07D 301/28; C07D 303/26
USPC ........................................................ 549/516
See application file for complete search history.

(56) References Cited

FOREIGN PATENT DOCUMENTS

| CN | 102060989 A | 5/2011 |
|---|---|---|
| JP | 42-20785 | 10/1967 |
| JP | 8-99968 | 4/1996 |
| JP | 2006-241081 | 9/2006 |
| JP | 2006241081 | * 9/2006 |
| JP | 4446651 | 1/2010 |
| JP | 2011-251941 | 12/2011 |
| WO | WO 2006/093281 A1 | 9/2006 |
| WO | WO 2010/064514 A1 | 6/2010 |

OTHER PUBLICATIONS

Morrison and Boyd, Organic Chemistry, 1983, 4th ed., p. 751(3 pages).*
Notification of Transmittal of Translation of the International Preliminary Report on Patentability mailed Feb. 6, 2014, for International Application No. PCT/JP2012/068115.
Office Action issued by the State Intellectual Property Office of the People's Republic of China on Aug. 14, 2014, in regards to Chinese application No. 201280036374.8.
Physical Organic Chemistry, 9 pgaes, by Yu Congxuan et al, Jul. 1991 Beijing Institute of Tech. p. 321-327.
Sun Mengzhou, et al., Synthesis and Characteristics of Hybrid Monomers with Different Chain Length for Cationic Photopolymorization; Paint & Coating Industry, vol. 37 No. 8, Aug. 2007, pp. 4-8.
Japanese Office Action, mailed Feb. 3, 2015, in Japanese Application No. 2011-160629 (translation and references cited therein previously submitted).
European Search Report, dated Nov. 17, 2014, in EP Application No. EP 12 81 7966.0, corresponding to PCT/JP2012/068115, citing WO 2006/093281.
Decision of Refusal dispatched by the Japan Patent Office on Jul. 21, 2015, in regards to Application No. 2011-160629.
Office Action issued Sep. 16, 2015, by the Taiwan Intellectual Property Office in regards to Application No. 10421254110.
Office Action issued Sep. 16, 2015, by the Taiwan Intellectual Property Office in regards to Application No. 101126126.

* cited by examiner

*Primary Examiner* — T. Victor Oh
(74) *Attorney, Agent, or Firm* — Fitch, Even, Tabin & Flannery, LLP

(57) ABSTRACT

A production method by which an alkyldiol monoglycidyl ether can be efficiently produced without requiring a complex purification step is provided. A method for producing an alkyldiol monoglycidyl ether, including a step of reacting a vinyl ether-containing alcohol with an epihalohydrin to form a vinyl ether-containing glycidyl ether, conducting a devinylation reaction in the presence of an acid catalyst and water, and further conducting an acetal decomposition reaction by adding an acid aqueous solution.

4 Claims, No Drawings

METHOD FOR PRODUCING ALKYLDIOL MONOGLYCIDYL ETHER

TECHNICAL FIELD

The present invention relates to a method for producing an alkyldiol monoglycidyl ether using a vinyl ether-containing alcohol.

BACKGROUND ART

Alkyldiol monoglycidyl ethers are useful as intermediates for medicaments, agrochemical raw materials and coating materials; and UV curable resins for electronic materials. As conventional methods for producing an alkyldiol monoglycidyl ether, in general, methods including reacting an alkanediol and an epihalohydrin using an alkali hydroxide are known (for example, see Patent Literatures 1 to 3). These production methods are generally steps including removing the by-produced salt by washing with water after the reaction, and conducting reflux under heating to thereby remove the epihalohydrin, water and the like. In this method, the original crude liquid contains a mixture of the raw material alkyldiol, and by-products such as an alkyldiol adduct and a dimer of an alkyldiol monoglycidyl ether and an alkyldiol diglycidyl ether, and thus it is difficult to isolate the objective product by the purification of these, and the yield is extremely low.

As a method for solving these problems, a method for obtaining an alkyldiol monoglycidyl ether by devinylating a vinyloxy group-containing glycidyl ether by reacting with a diol in the presence of an acid catalyst is known (for example, see Patent Literature 4).

CITATION LIST

Patent Literatures

Patent Literature 1: JP 42-20785 A
Patent Literature 2: JP 8-99968 A
Patent Literature 3: JP 4446651 B1
Patent Literature 4: JP 2006-241081 A

SUMMARY OF INVENTION

Technical Problem

However, the method described in the above-mentioned Patent Literature 4 is not efficient, since a diol in an equivalent amount to that of the raw material used is required, and a high temperature and a condition close to vacuum are required for removing the acetal compound that is by-produced from the diol. Furthermore, a problem that an acetal-type glycidyl ether dimer having a high boiling point derived from the diol compound is generated has been clarified by an additional test by the present inventors.

The present invention aims at providing a production method by which an alkyldiol monoglycidyl ether can be efficiently produced at a high purity and a high yield without requiring a complex purification step.

Solution to Problem

The present inventors did various studies, and consequently found that an alkyldiol monoglycidyl ether can be efficiently obtained by a devinylation method including glycidylating a vinyl ether-containing alcohol to form a vinyl ether-containing alkyl glycidyl ether, and allowing co-presence of water in the presence of an acid catalyst. Furthermore, the present inventors also found that an acetal-type glycidyl ether dimer is generated as a by-product in the devinylation reaction, whereas the glycidyl ether dimer is decomposed by adding an aqueous solution of an acid after the devinylation reaction, and an alkyldiol monoglycidyl ether can be obtained.

Specifically, the present invention is as follows.

(1) A method for producing an alkyldiol monoglycidyl ether, including a step of reacting a vinyl ether-containing alcohol with an epihalohydrin to form a vinyl ether-containing glycidyl ether, conducting a devinylation reaction in the presence of an acid catalyst and water, and further conducting an acetal decomposition reaction by adding an acid aqueous solution.

(2) The method for producing an alkyldiol monoglycidyl ether according to the above-mentioned (1), wherein the pressure in the reaction system of the devinylation reaction is 50 kPa or less.

(3) The method for producing an alkyldiol monoglycidyl ether according to the above-mentioned (1) or (2), wherein the temperature in the reaction system in the devinylation reaction and acetal decomposition reaction is 10° C. to 60° C.

(4) The method for producing an alkyldiol monoglycidyl ether according to any one of the above-mentioned (1) to (3), wherein the pressure in the reaction system in the acetal decomposition reaction is 20 kPa or less.

(5) The method for producing an alkyldiol monoglycidyl ether according to any one of the above-mentioned (1) to (4), wherein the vinyl ether-containing alcohol is represented by the following general formula (I):
[Chemical Formula 1]

$$CH_2=CH-O-R-OH \qquad \text{General Formula (I)}$$

wherein R represents a straight chain or alicyclic alkylene group, or a straight chain or alicyclic alkenylene group.

(6) The method for producing an alkyldiol monoglycidyl ether according to any one of the above-mentioned (1) to (5), wherein the vinyl ether-containing alcohol is 4-hydroxybutyl vinyl ether.

Advantageous Effects of Invention

According to the present invention, a production method by which an alkyldiol monoglycidyl ether can be efficiently produced at a high purity and a high yield without undergoing a complex purification step such as distillation can be provided.

DESCRIPTION OF EMBODIMENTS

Embodiments for carrying out the method for producing an alkyldiol monoglycidyl ether according to the present invention will be explained in detail.

The method for producing an alkyldiol monoglycidyl ether according to the present invention includes a step of glycidylating a vinyl ether-containing alcohol to form a vinyl ether-containing glycidyl ether, conducting a devinylation reaction in the presence of an acid catalyst and water, and further conducting an acetal decomposition reaction by adding an acid aqueous solution.

In the present invention, at first, the hydroxyl group of the vinyl ether-containing alcohol is glycidylated to give a vinyl ether-containing glycidyl ether. A glycidylation reaction method cannot be applied to a method using an acid catalyst since the vinyl group is reacted, but a generally-utilized method can be applied as long as it is a reaction with an epihalohydrin using an alkali metal hydroxide.

Examples of the vinyl ether-containing alcohol used in the present invention may include compounds represented by the following general formula (I) such as 4-hydroxybutyl vinyl ether, 6-hydroxyhexyl vinyl ether, 9-hydroxynonyl vinyl ether, 10-hydroxydecanyl vinyl ether, 12-hydroxydodecyl vinyl ether, cyclohexanedimethanol monovinyl ether and cyclohexenedimethanol monovinyl ether.

[Chemical Formula 2]

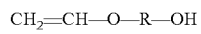   General Formula (I)

wherein R represents a straight chain or alicyclic alkylene group, or a straight chain or alicyclic alkenylene group.

R in the general formula (I) represents a straight chain or alicyclic alkylene group, or a straight chain or alicyclic alkenylene group, and the straight chain alkylene group is preferably one having a carbon number of 2 to 20, the alicyclic alkylene group is preferably one having a carbon number of 2 to 20, the straight chain alkenylene group is preferably one having a carbon number of 2 to 20, and the alicyclic alkenylene group is preferably one having a carbon number of 2 to 20.

Examples of the alkali metal hydroxide used in the glycidylation reaction according to the present invention may include, but are not specifically limited to, potassium hydroxide and sodium hydroxide. As the use amount of those, 1 or more equivalent amount, preferably 1 to 2 equivalent amount is required with respect to the vinyl ether-containing alcohol. In the case when the use amount is less than 1 equivalent amount, the reaction stops in midstream, whereas in the case when the use amount exceeds 2 equivalent amount, a side reaction easily occurs, and thus the purity tends to decrease.

The epihalohydrin used in the present invention is preferably epichlorohydrin due to its easy availability. Furthermore, the use amount is 1 or more equivalent amount, preferably 1 to 10 equivalent amount with respect to the vinyl ether-containing alcohol. In the case when the use amount is less than 1 equivalent amount, the reaction stops in midstream, whereas in the case when the use amount exceeds 10 equivalent amount, a side reaction easily occurs, and thus the purity tends to decrease.

In the glycidylation reaction, a catalyst such as a quaternary ammonium salt can also be used. As the quaternary ammonium salt used, general quaternary ammonium salts such as benzyltrimethylammonium chloride, benzyltriethylammonium chloride, tetramethylammonium chloride and tetraethylammonium chloride can be used.

After the vinyl ether-containing glycidyl ether is obtained by the glycidylation reaction, distillation purification may further by conducted. The method for distillation purification depends on the boiling point of the vinyl ether-containing glycidyl ether, and distillation under a reduced pressure is generally suitable.

The devinylation reaction according to the present invention is conducted by allowing the co-presence of water in the presence of an acid catalyst. The acetaldehyde generated during the devinylation reaction can be removed by reducing the pressure in the reaction system, and a part of the acetaldehyde is taken into the water and reacts with the alkyldiol monoglycidyl ether generated by the devinylation reaction to form an alkyldiol monoglycidyl ether methylacetal (an acetal dimer). In the case when the acetal dimer remains, defects such as increase in viscosity due to a crosslinking reaction and gelation are caused when the substance obtained by the present invention is polymerized and used. However, the acetal dimerization reaction is a reversible reaction, and the acetal dimer is easily decomposed under an acid catalyst; therefore, in the present invention, the acetal dimer is decomposed by conducting an acetal decomposition reaction mentioned below after the devinylation reaction.

Examples of the acid catalyst that can be used in the devinylation reaction according to the present invention may generally include sulfuric acid, sodium hydrosulfate, paratoluenesulfonic acid, benzenesulfonic acid, methanesulfonic acid and solid acids (zeolite, Amberlite, Amberlist, Nafion and the like). Furthermore, the amount of the catalyst used is preferably 0.1 to 10 mass % with respect to the vinyl ether-containing glycidyl ether to be reacted, and is more preferably 0.5 to 2 mass % in view of reactivity. In the case when the amount of the catalyst used is less than 0.1 mass %, the devinylation reactivity significantly decreases, and thus the reaction extremely slows. Furthermore, in the case when the amount is more than 10 mass %, many by-products including acetal dimers, and open-ring and polymerization of the glycidyl group are generated.

The use amount of the water in the devinylation reaction according to the present invention is not specifically limited as long as the amount is in an equal molar amount or more with respect to the vinyl ether-containing glycidyl ether, the devinylation reaction quickly progresses and the production amount of the acetal dimer can be suppressed by using the water by preferably 20 to 60 mass % with respect to the vinyl ether-containing glycidyl ether. When the use amount of the water is less than 20 mass % with respect to the vinyl ether-containing glycidyl ether, the amounts of the by-products such as an acetal dimer and open-ring and polymerized products of the glycidyl group increase, whereas when the use amount exceeds 60 mass %, the devinylation reaction slows. Furthermore, when the use amount is less than an equivalent molar, the progress of the devinylation reaction stops in midstream.

The devinylation reaction according to the present invention is an exothermal reaction, and thus it is necessary to remove the acetaldehyde generated by the reaction by reducing the pressure in the system. It becomes possible to obtain a high purity alkyldiol monoglycidyl ether in which gelation and by-products are suppressed, by controlling the reaction temperature to 60° C. or less, preferably 20° C. to 50° C. The method for controlling the reaction temperature may include a method including cooling the reactor, or gradually adding the vinyl ether-containing glycidyl ether to the aqueous solution of the catalyst. Furthermore, after the heat generation is completed, warming is conducted in a hot bath or the like so as to keep the temperature. When the reaction temperature is in the range of 20° C. to 50° C., the acetaldehyde can be removed from the reaction system by setting the pressure in the system to 50 kPa or less. In order to efficiently promote the devinylation reaction, the pressure in the system is more preferably 30 kPa or less.

The present invention includes further conducting an acetal decomposition reaction by adding an acid aqueous solution after the devinylation reaction has been conducted. As the acid aqueous solution, aqueous solutions of the acids as exemplified in the explanation on the above-mentioned acid catalyst can be used. Furthermore, the addition amount of the acid aqueous solution at this time is, but not specifically limited to, preferably 0.1 to 10 mass % on the basis of the vinyl ether-containing glycidyl ether. Furthermore, the concentration of the acid aqueous solution is, but not specifically limited to, preferably 0.01 mass % to 5 mass %. In the case when the amount and concentration of the acid in the acetal decomposition reaction are out of these ranges, it is possible that the decomposition reaction significantly slows, or by-products are generated.

As the method for adding the acid aqueous solution in the acetal decomposition reaction according to the present invention, either a method including gradually adding dropwise or a method including adding at once is available. Furthermore, for the pressure in the reaction system during the acetal decomposition, although the condition for the devinylation reaction can be continuously conducted, it is preferable to set the pressure in the system to, preferably 20 kPa or less, more preferably 10 kPa or less, so as to allow rapid progress of the reaction.

After the acetal decomposition reaction is completed, it is necessary to remove the acid catalyst by neutralizing with a base. Examples of the base may include hydroxides or salts of alkali metals or alkaline earth metals such as potassium hydroxide, sodium hydroxide, potassium carbonate, sodium carbonate, potassium hydrogen carbonate and sodium hydrogen carbonate. Furthermore, in removing the aqueous layer by separation after the neutralization, in order to improve the separability, solvents such as toluene and xylene can be used alone or by combining two or more kinds, or a method for increasing the specific gravity of the aqueous layer by adding sodium chloride or the like can be used.

After the neutralization, the excess water content, and the solvent, in the case when the solvent is used, are distilled off by concentration. The concentration is preferably conducted under an ordinary pressure or a reduced pressure while keeping the liquid temperature at 90° C. or less, more preferably in the range of 65° C. to 85° C. When the liquid temperature exceeds 90° C., it is highly possible that the coloring or decomposition of the alkyldiol monoglycidyl ether is caused.

After the concentration, the residual insoluble components such as a neutralized salt can be removed by conducting filtration. During the filtration, it is preferable to use a filtration aid such as diatomite so as to efficiently remove the insoluble components.

Since the method for producing an alkyldiol monoglycidyl ether according to the present invention can provide an alkyldiol monoglycidyl ether by conducting a devinylation reaction and an acetal decomposition reaction using water, any purification step other than the filtration is not necessary; however, where necessary, a general purification method such as distillation can be conducted.

EXAMPLES

Hereinafter the present invention will further be specifically explained by Examples, but the present invention is not limited to the following Examples.

Example 1

(Synthesis of Vinyloxybutyl Glycidyl Ether)

1,000 g (8.61 mol) of 4-hydroxybutyl vinyl ether (HBVE manufactured by Maruzen Petrochemical) and 448 g (11.2 mol) of sodium hydroxide were charged in a 3 L cylindrical flask equipped with a stirrer, a thermometer and a dropping funnel. The temperature was raised to 40° C. under stirring, 1,243 g (13.4 mol) of epichlorohydrin was then gradually added, and a reaction was conducted under controlling to 40° C. to 60° C. At after 8 hours of the reaction, the sodium chloride generated by the reaction was removed by filtration, 1,000 g of hexane was put therein, and the mixture was washed with 400 g of a 3% aqueous solution of sodium hydrogen sulfate and further washed with 800 g of 17% brine. The organic layer was concentrated by using a rotary evaporator to thereby distill the hexane off, and filtration was conducted to give the objective vinyloxybutyl glycidyl ether with a purity of 94% and a yield of 94%. At this time, the 4-hydroxybutyl vinyl ether contained in the obtained substance was 0.5%.

(Synthesis of Butanediol Monoglycidyl Ether)

5.0 g of paratoluenesulfonic acid and 140 g of pure water were charged in a 1 L four-necked separable flask, and a vacuum pump equipped with a stirrer, a thermometer, an air introduction tube and a cooling trap was installed. Under stirring, 500 g of the vinyloxybutyl glycidyl ether synthesized above was slowly added to the flask while the liquid temperature was adjusted so as to be kept at 40° C. After the addition was completed, the pressure was reduced to 20 kPa, and stirring was continued for 1 hour while dry air was introduced at 100 ml/min. The reaction solution was then analyzed by gas chromatography, and no peak of the vinyloxybutyl glycidyl ether was observed. However, since 5.2% of an acetal dimer was generated according to an analysis by liquid chromatography, 26 g of a 0.04% aqueous solution of paratoluenesulfonic acid was added, and an acetal decomposition reaction was conducted at a pressure of 5 kPa while the temperature was kept at 40° C. When the reactant was analyzed 1 hour after the reaction, the peak of the acetal dimer had almost disappeared, and thus the reaction was quenched. 2.1 g of sodium hydrogen carbonate was put into the solution in which the reaction had been completed to thereby neutralize the solution, and the water in the system was distilled off by concentration with a rotary evaporator, the water content in the system was confirmed to be 800 ppm or less, and the concentrated liquid was filtered to give the objective butanediol monoglycidyl ether with a purity of 92% and a yield of 99%. At this time, the butanediol contained in the obtained substance was 0.2%, and no acetal dimer was detected.

Example 2

Similar operations to those in Example 1 were conducted, except that vinyloxybutyl glycidyl ether was synthesized and then subjected to distillation under a reduced pressure and used for the synthesis of butanediol monoglycidyl ether. The distillation under a reduced pressure was conducted at a pressure of 0.4 kPa, and the distillation temperature was 82° C. The obtained purified vinyloxybutyl glycidyl ether had a purity of 99% and a yield of 94%. Furthermore, the finally obtained butanediol monoglycidyl ether by devinylation and acetal decomposition was obtained with a purity of 95% and a yield of 99%. At this time, the butanediol included in the obtained substance was 0.1%, and no acetal dimer was detected.

The butanediol in the butanediol monoglycidyl ethers obtained in the methods of Examples 1 and 2 was 0.2% or less, and no butanediol diglycidyl ether was detected.

Comparative Example 1

(Method for Synthesis from Butanediol)

300 g (3.3 mol) of 1,4-butanediol and 132 g (3.3 mol) of sodium hydroxide were charged in a 1 L flask equipped with a stirrer, a stirrer, a thermometer and a dropping funnel. The temperature was raised to 40° C. under stirring, thereafter 305 g (3.3 mol) of epichlorohydrin was gradually added, and a reaction was conducted while the temperature was controlled to 40° C. to 60° C. After the reaction for 3 hours, when the reaction solution was analyzed by gas chromatography, the reaction rate of the 1,4-butanediol was 45%. This reaction solution was extracted five times with 600 g of water and 300 g of ethyl acetate, and the organic layer was further washed twice with 200 g of water. The organic layer was concentrated in a rotary evaporator to distill the ethyl acetate off, and filtration was conducted to give the objective butanediol monoglycidyl ether with a purity of 87% and a yield of 41%. At this time, the butanediol included in the obtained substance was 4% and the diglycidyl ether was 5%, and plural unclear components were further detected by gas chromatography.

Since butanediol diglycidyl ether and other by-products are generated and 1,4-butanediol remains in the method for synthesis from 1,4-butanediol as in Comparative Example 1, plural times of extraction operations are required, and the obtained substance has a low purity unless distillation and purification are conducted.

Comparative Example 2

(Method Described in Patent Literature 4 Mentioned Above)

31.0 g of ethylene glycol and 0.03 g of paratoluenesulfonic acid were charged in a 300 ml four-necked flask, and a vacuum pump equipped with a stirrer, a thermometer, an air introduction tube and a cooling trap was installed. Under stirring, 79 g of the vinyloxybutyl glycidyl ether synthesized in Example 1 was slowly added to the flask at a reaction pressure of 10 kPa while the liquid temperature was adjusted so as to be kept at 35° C. The ethylene glycol methyl acetal generated in accordance with the progress of the reaction was continuously distilled off. The reaction conversion was 23% by the reaction for 3 hours; therefore, 0.3 g of paratoluenesulfonic acid was additionally added and the reaction was conducted, and the reaction conversion became 100% at 1 hour after the addition. Stirring was further conducted for 4 hours until the generated ethylene glycol methyl acetal was not detected on gas chromatography, 0.5 g of magnesium oxide was added to effect neutralization, and filtration was conducted. The objective butanediol monoglycidyl ether was obtained at a purity of 88% and a yield of 94%. At this time, 5.5% of a peak that was considered to be a reaction product of the butanediol monoglycidyl ether and ethylene glycol methyl acetal was detected in the obtained substance by an analysis by liquid chromatography.

In Comparative Example 2, ethylene glycol is excessively used, and a reactant with the by-produced ethylene glycol methyl acetal is generated and thus the purity is lowered.

Comparative Example 3

5.0 g of paratoluenesulfonic acid and 140 g of pure water were charged in a 1 L four-necked separable flask, and a vacuum pump equipped with a stirrer, a thermometer, an air introduction tube and a cooling trap was installed. Under stirring, 500 g of the vinyloxybutyl glycidyl ether synthesized in Example 1 was slowly added to the flask while the liquid temperature was adjusted so as to be kept at 40° C. After the addition was completed, the pressure was reduced to 20 kPa, stirring was continued for 1 hour while dry air was introduced at 100 ml/min. The reaction solution was then analyzed by gas chromatography, and no peak of vinyloxybutyl glycidyl ether was observed. 2.1 g of sodium hydrogen carbonate was put into the reaction solution to effect neutralization, the water in the system was distilled off by concentration in a rotary evaporator, and it was confirmed that the water content in the system was 800 ppm or less. The concentrated liquid was filtered to give the objective butanediol monoglycidyl ether with a purity of 85% and a yield of 99%. At that time, the butanediol contained in the obtained substance was 0.2%, and the acetal dimer was 7.2%.

Comparative Example 3 was different from Example 1 in that an acetal decomposition reaction was not conducted, and thus the acetal dimer was naturally left, and the purity of the synthesized butanediol monoglycidyl ether was inferior to those of Examples 1 and 2.

Comparative Example 4

5.0 g of paratoluenesulfonic acid and 140 g of pure water were charged in a 1 L four-necked separable flask, and a vacuum pump equipped with a stirrer, a thermometer, an air introduction tube and a cooling trap was installed. Under stirring, 500 g of the vinyloxybutyl glycidyl ether synthesized in Example 1 was slowly added to the flask while the liquid temperature was adjusted so as to be kept at 40° C. After the addition was completed, the pressure was reduced to 20 kPa, stirring was continued for 1 hour while dry air was introduced at 100 ml/min. Thereafter, when the reaction solution was analyzed by gas chromatography, no peak of vinyloxybutyl glycidyl ether was observed. However, according to an analysis by liquid chromatography, 5.3% of an acetal dimer was generated. Therefore, 26 g of pure water was added, the pressure was set to 5 kPa, and an acetal decomposition reaction was conducted. When an analysis was conducted 1 hour after the reaction, the peak of the acetal dimer was 5.2% and thus was changed little. Furthermore, even the reaction was then conducted, the peak of the acetal dimer was not decreased.

Comparative Example 5

5.0 g of paratoluenesulfonic acid and 140 g of pure water were charged in a 1 L four-necked separable flask, and a vacuum pump equipped with a stirrer, a thermometer, an air introduction tube and a cooling trap was installed. Under stirring, 500 g of the vinyloxybutyl glycidyl ether synthesized in Example 1 was slowly added to the flask while the liquid temperature was adjusted so as to be kept at 40° C. After the addition was completed, the pressure was reduced to 20 kPa, stirring was continued for 1 hour while dry air was introduced at 100 ml/min. Thereafter, when the reaction solution was analyzed by gas chromatography, no peak of vinyloxybutyl glycidyl ether was observed. However, according to an analysis by liquid chromatography, 5.3% of an acetal dimer was generated. Therefore, 0.05 g of paratoluenesulfonic acid was added, the pressure was set to 5 kPa, and an acetal decomposition reaction was conducted. When an analysis was conducted 1 hour after the reaction, the peak of the acetal dimer was 5.1% and thus was changed little. Furthermore, even the reaction was then conducted, the peak of the acetal dimer was not decreased.

Comparative Examples 4 to 5 each corresponds to an acetal decomposition reaction and is an example in which an acid or water is used alone. Since decomposition did not occur in both cases, it is understood that addition of an acid aqueous solution is necessary for acetal decomposition.

The invention claimed is:
1. A method for producing a monoglycidyl ether of an alkylene diol or alkenylene diol, comprising the steps of:
   reacting a vinyl ether-containing alcohol with an epihalohydrin, to form a vinyl ether-containing glycidyl ether,
   subjecting the vinyl ether-containing glycidyl ether to a devinylation reaction in the presence of an acid catalyst and water, removing acetaldehyde produced by the devinylation reaction while maintaining a reaction pressure of 50kPa or less and a reaction temperature of 20 to 50° C, and further conducting an acetal decomposition reaction by adding an acid aqueous solution, wherein the vinyl ether-containing alcohol is represented by the following formula (I):

$$CH_2=CH-O-R-OH \qquad \text{Formula (I)}$$

wherein R represents a straight chain or alicyclic alkylene group having a carbon number of 2 to 20, or a straight chain or alicyclic alkenylene group having a carbon number of 2 to 20.

2. The method for producing a monoglycidyl ether of an alkylene diol or alkenylene diol according to claim 1, wherein the pressure in the reaction system in the acetal decomposition reaction is 20 kPa or less.

3. The method for producing a monoglycidyl ether of an alkylene diol or alkenylene diol according to claim 1, wherein the vinyl ether-containing alcohol is 4-hydroxybutyl vinyl ether.

4. The method for producing a monoglycidyl ether of an alkylene diol or alkenylene diol according to claim 1, wherein the devinylation reaction is conducted in the presence of 20 to 60 mass % percent water with respect to the vinyl ether-containing glycidyl ether.

* * * * *